United States Patent [19]

Petrow

[11] Patent Number: 4,581,229

[45] Date of Patent: Apr. 8, 1986

[54] METHOD OF REMOVING METAL IONS AND COMPOUNDS FROM THE HAIR

[76] Inventor: Henry Petrow, 32 Garfield St., Watertown, Mass. 02172

[21] Appl. No.: 604,977

[22] Filed: Apr. 27, 1984

Related U.S. Application Data

[63] Continuation of Ser. No. 460,983, Jan. 23, 1983, abandoned.

[51] Int. Cl.$^4$ .......................... A61K 7/06; A61K 7/08
[52] U.S. Cl. ........................................ 424/70; 8/127.5; 8/127.51; 132/7; 252/89.1; 252/133; 424/127
[58] Field of Search ................. 424/70, 127; 252/89.1, 252/133; 8/127.51, 127.5; 132/7

[56] References Cited

U.S. PATENT DOCUMENTS 3,840,401 10/1974 Umezawa et al. ............... 8/127.51

FOREIGN PATENT DOCUMENTS 0037224 10/1981 European Pat. Off. ............ 424/70

OTHER PUBLICATIONS

Faircher et al., "Sorption and Desorption of a Cationic Polymer by Human Hair: Effects of Salt Solutions", Fex Res Jour, 1978, pp. 616–620.

*Primary Examiner*—Dale R. Ore
*Attorney, Agent, or Firm*—Pennie & Edmonds

[57] ABSTRACT

A hair treating solution and method are provided for improving hair quality and aiding in removal of inorganic substances from hair. Metals such as copper, iron, manganese, nickel and the like, if attached to hair after swimming or other hair-exposure thereto, can be removed by the use of soluble lanthanum salt in a simple rinsing method.

12 Claims, No Drawings

METHOD OF REMOVING METAL IONS AND COMPOUNDS FROM THE HAIR

CROSS REFERENCE TO RELATED APPLICATION

This application is a continuation of application Ser. No. 460,983, filed Jan. 23, 1983, now abandoned.

BACKGROUND OF THE INVENTION

It is well-known that swimmers and others who expose hair to various metal ions and compounds can experience certain problems. Hair can appear to have green, reddish, blue or other colors after exposure to and interaction with certain waters. For example, iron, copper, maganese, nickel and other metal ions and compounds if present in water can deposit in the hair of swimmers and other people exposing their hair to this water. Normal shampoos and rinses often have difficulty in removing such deposits.

While chlorine removal methods and products are known and successful as described in U.S. Pat. No. 4,295,985, common, well-accepted means and methods for easily and efficiently removing metal ions and compounds from human or other hair have been difficult to find.

SUMMARY OF THE INVENTION

It is an object of this invention to provide a means and method for removing and avoiding metallic compound deposits in the hair.

Another object of this invention is to provide a means and method for treating the hair to improve appearance, texture, and elasticity and yield hair which better accepts normal permanent waving processing.

Still another object of this invention is to provide a lanthanum salt solution which aids in removing or desorbing metallic compound deposits from hair rapidly and efficiently.

According to the invention a hair-treating solution has an aqueous base having incorporated therein from 0.5% by weight to saturation of a water-soluble lanthanum salt. Preferably the solution has a pH of from 3.0 to 8.3. The normality of the lanthanum in solution is at or above 0.04 Normal.

In preferred embodiments, a lanthanum salt is incorporated in other normal hair-treating solutions. For example, the lanthanum salt is preferably incorporated in a shampoo or conditioner. The hair can be shampooed and/or conditioned and simultaneously treated to prevent metallic compounds from being retained by the hair.

According to a method of treating hair in accordance with this invention an aqueous solution containing from about 0.5% by weight to saturation of a water soluble lanthanum salt is applied to the hair and then rinsed. The normality of the lanthanum in solution is at or above 0.04 Normal.

The lanthanum salt acts to desorb metallic compound deposits. Surprisingly the lanthanum salt also acts to render the hair better prepared for permanent waving and acts to improve properties of the hair. Often appearance, texture, elasticity and other hair properties are improved. The lanthanum salt further acts to avoid substantial swelling of the hair as might otherwise occur when exposed to various hair-treating solutions. In general the trivalent lanthanum cations desorb colored ions from hair and otherwise improve hair quality.

DESCRIPTION OF PREFERRED EMBODIMENT

An active agent in the form of a water soluble lanthanum salt can be incorporated with any hair treatment product. The product must not adversely affect the action of the lanthanum salt, as by insolubilizing lanthanum or forming strong complexes with lanthanum to reduce the trivalent charge, or otherwise interfere with the presence of appreciable concentration of positively trivalent active agent. Materials to be avoided in combination with the lanthanum salt in products for use in the treating solutions and method of this invention are products such as soaps, fatty acids, chelating and complexing agents, phosphates, carbonates and the like. The materials to be avoided are those that make the lanthanum insoluble or combine with it to reduce its positively trivalent charge.

The lanthanum salt used can be any of the known water-soluble lanthanum salts which are soluble in water or aqueous solutions at standard room temperature. Such salts include lanthanum chloride, sulfate, acetate, nitrate, bromide and the like. However, lanthanum sulfate has been found to be particularly effective.

The lanthanum salt can be used in a pH range of from 3.0 to 8.3 at all normal pHs at which solutions are applied to human hair. Thus the treatment can occur at ranges of from pH 4.5 to 7.5 which is the normal pH range for shampoos. When mixed with conditioners, pHs of 4 to 5 are preferred.

The lanthanum salt can be in its hydrated forms as for example lanthanum sulfate hydrate $La_2(SO_4)_3 \cdot 9H_2O$. The lanthanum sulfate hydrate which is the preferred salt for use in this invention is preferably in an amount of from 0.5% by weight to 2.0% by weight of the aqueous solution corresponding to 0.04 Normal to 0.16 Normal. However, lanthanum salts in amounts of from 0.5% by weight to the saturation point of the water-soluble lanthanum salt used can be employed in the methods and solutions of this invention.

Simple hair-treating solutions comprise the use of the lanthanum salt in a range of from 0.5% by weight of the total solution to saturation of a water solution, used at room temperature to rinse the hair after exposure to water, as in swimming, showering, bathing, etc. or after metallic ion and compound contamination as by exposure to hair rinses of various sorts.

The treating solution can be applied to the hair for periods of 20 seconds to 20 minutes or longer and then rinsed from the hair with tap water, all at room temperature. If desired, the solutions and the rinse water can be heated to normal human showering water temperatures although there is no need for heating. The reactions of the lanthanum salt with metal ions which may be absorbed into the hair, is rapid and often occurs in seconds, In some cases, when incorporated in shampoos, it is preferred to use the treating solution in an application to the hair for periods of from 20 seconds to as long as one hour in order to ensure thorough reaction with the metal ions or compounds attached to the hair.

The shampoos, conditioners and other solutions into which the lanthanum salt can be incorporated are numerous and include those known to the art so long as they do not contain ingredients or impurities which insolubilize or form strong complexes with the lanthanum or otherwise substantially reduce the proportion of trivalent lanthanum present as the positively trivalent species.

For example, suitable shampoo solutions are described in U.S. Pat. No. 4,295,985. Such shampoos and hair-cleaning solutions include surfactants or detergents which may have chlorine-reducing agents incorporated therewith. Those shampoos which have glycol sterate or other materials noted above to be avoided should not be used.

The detergents as used herein are those which are well-known in the art for hair shampoo and conditioner uses and can be defined as synthetic water-soluble cleansing preparations that emulsify oils and hold dirt in suspension. Typical examples of detergents useful in this invention include, but are not limited to, lauramide DEA, sodium laureth sulfate, sodium lauryl sulfate, triethanolamine lauryl sulfate, and ammonium lauryl ether sulfate.

When chlorine-removing shampoos are used, as described in the above-noted patent, chlorine-reducing agents can be incorporated in the solution in amounts of from 2% to 15% by weight of the detergent in the shampoo and from about 0.4% to 6% by weight of the entire liquid composition which comprises a detergent and water. Such reducing agents include non-toxic, non-skin irritating reducing agents compatible with detergents and soluble in water. Preferred reducing agents include alkali metal thiosulfates, alkali metal nitrites and alkali metal sulfites. Sodium thiosulfate is a preferred reducing agent while other specific reducing agents include, but are not limited to, sodium sulfite, sodium hydro sulfite, urea, sodium nitrite, ascorbic acid, and others. Other typical additives to conditioners and shampoos can be incorporated in the aqueous solutions of this invention so long as they do not adversely affect the lanthanum as described above. Mixtures of one or more reducing agents, detergents and lanthanum salts can also be used.

Typical additives include fragrances such as PFW #800471 from Pollak's Fruital Works, Inc. of Middletown, New York and Fragrance #32-329 from Alpine Aromatics International, Inc. of Metuchen, N.J. Whitening and coloring agents such as titanium dioxide and emollients such as lanolin, methyl-gluceth-20, mineral oil, aliphatic alcohols and methyl glucocide alkoxlates can be used. Solubilizers such as SD alcohol 3A and conditioners such as hydrolyzed animal protein along with preservatives such as formaldehyde, methylparaben and propylparaben are also useful.

Such materials are often admixed in amounts by weight of the total composition as follows in a general shampoo formulation:

fragrances—0 to 5%
coloring agents—0 to 8%
emollients—0 to 15%
solubilizer—0 to 5%
hydrolyzed protein—0 to 5%
preservatives—0.4 to 3%
water—60 to 85%
detergent—10 to 35%
lanthanum salt—0.5 to 2.0%

In a general conditioner formulation the following are used in percent by weight of the entire composition:
fragrances—0 to 5%
coloring agents—0 to 8%
emollients—0 to 15%
hydrolyzed protein—0 to 5%
quaternary ammonium compound—1 to 20%
thickening agent—0 to 2%
preservative—0.4 to 3%
water—60 to 90%

The conditioners as known in the art contain one quaternary ammonium compound bearing one or two long alkyl chains. These compounds are known as alkonium chlorides such as stearalkonium chloride and further include, but are not limited to, stearyl dimethyl benzyl ammonium chloride, cetyl dimethyl benzyl ammonium chloride, n-alkyl dimethyl benzyl ammonium chloride, Merquat (polyquaternium) and Celquat H-100 (cationic polymer quaternary cellulose derivative.) The positively charged quarternaries become firmly attached to the surface of hair, reducing its tendency to develop a static charge and decreasing hair-to-hair and hair-to-comb friction. The conditioners always contain the quaternary alkonium compound but may eliminate the hydrolyzed protein in some cases. The thickening agents include natural gum, i.e., acacia, guar, methyl cellulose, carboxy methyl cellulose, aluminum silicate and polyvinyl pyrrolidone.

In general a wide-variety of aqueous solutions can incorporate therein the lanthanum salts of this invention to provide the hair-enhancing and metal compound removing and desorbing properties of the lanthanum salt when used in the treatment of human hair.

The following examples are illustrative of the invention and are not to be considered as limiting thereof.

EXAMPLE 1

This example indicates specific procedures for removal of iron from white human hair.

Ten one-gram sample tresses of white human hair obtained from DeMeo Bros., New York, were subjected to chlorination treatment consisting of 15 minute soaking in water containing 13.5 ppm chlorine (NaOCl added as 5.25% solution).

During this exposure chemical interaction between hair and the oxidant was apparent as the pH slowly decreased with time. Following the removal of the hair from the chlorine-containing bath, spot tests indicated there was still unconsumed chlorine contained in the bath.

These hair samples were well washed in distilled water. These well-washed samples were then exposed for 15 minutes in a well-stirred dispersion of 6 ppm ferric oxide which was added as colloidal iron oxide. After the 15 minute treatment, the samples were rinsed in distilled water and dried. All samples, following this treatment, had the easily-observed reddish-brown hue that resulted from the adsorbed iron oxide.

Two of these samples without further treatment were analyzed for their ferric oxide content and found to contain in one case 172 ppm and in the other 159 ppm expressed as iron. A control sample of this hair which had received no ferric oxide treatment whatsoever contained 28 ppm iron.

Samples of the iron-containing hair were washed in either one of the following products:
(1) Agree, a popular shampoo product, produced by S. C. Johnson & Sons, Inc. of Racine, Wisconsin,
(2) a shampoo of the formula indicated in Table 1,
(3) a shampoo of the formula indicated in Table 1 excepting it contained no lanthanum, and (4) a conditioner of the formula indicated in Table 2.

TABLE 1

| Ingredient | Wt. % |
| --- | --- |
| water | 78.00 |
| sodium laureth sulfate | 15.00 |
| lauramide DEA | 4.00 |
| lanthanum sulfate hydrate | 1.20 |
| hydrolyzed animal protein | 1.00 |
| formaldehyde | 0.40 |
| fragrance | 0.25 |
| methylparaben | 0.18 |
| propylparaben | 0.02 |

TABLE 2

| Ingredient | Wt % |
| --- | --- |
| water | 86.00 |
| stearalkonium chloride | 7.00 |
| glycerine | 3.00 |
| hydrolyzed animal protein | 1.00 |
| sodium chloride | 1.00 |
| PPG-20 (methyl glucose ether) | 0.50 |
| lanthanum sulfate hydrate | 0.50 |
| formaldehyde | 0.40 |
| methylparaben | 0.20 |
| perfume | 0.20 |
| propylparaben | 0.05 |

The results with respect to iron removal are presented in Table 3 where the hair washed for 30 seconds has starting iron concentration of 28 PPM for untreated hair and 159 or 172 PPM iron for treated unwashed hair.

TABLE 3

| washing product | Residual iron, PPM in hair |
| --- | --- |
| Agree | 131 |
| Table 1 formula | 48 |
| Table 1 formula minus lanthanum sulfate | 88 |
| Table 2 conditioner | 37 |

Using white hair, iron deposition and efficacy of removal are easily observed visually so that qualitative comparisons of the effect of lanthanum sulfate concentration could be easily made. These observations indicated that lanthanum sulfate hydrate levels as low as 0.5% were still efficacious to an observable degree, whereas, the sample washed in Agree, was visually undistinguishable from unshampooed controls.

Lanthanum chloride is a more soluble lanthanum salt than the sulfate and is commercially more readily available. However, lanthanum chloride is not as effective as the sulfate for iron removal at equivalent concentrations.

EXAMPLE 2

One-gram sample tresses of white hair were subjected to the identical chlorine treatment described above in Example 1. The hair samples were well-washed and then exposed for 15 minutes to 50 ppm copper added as cupric chloride. These samples were then washed with distilled water. On drying, the well-known green hair syndrome was easily observable. These hair samples were variously washed with one of the following solutions: (1) Johnson's Baby Shampoo, a product of Johnson & Johnson, of Skillman, N.J., (2) Johnson's Baby Shampoo, plus 1.5% lanthanum chloride hydrate, (3) UltraSwim Shampoo, a commercially available chlorine-removal shampoo of Eljenn International Corp. of Newton, Mass., containing urea and sodium thiosulfate as the active chlorine-reducing agents, or, 4) the shampoo of Table 1 with lanthanum.

The efficacy of the various treatments could be estimated visually without the use of instrumentation. Johnson's Shampoo with and without lanthanum produced no observable reduction of the green coloration. It was observed that when the lanthanum salt was added to the Johnson's shampoo it became nearly opaque and the viscosity increased to a gel-like state. It is theorized that the lanthanum was insolubilized or reduced in valence by an ingredient in the shampoo. UltraSwim Shampoo produced a small diminution of the green coloration, but a decidedly green coloration remained. The shampoo formulation in Table 1 produced a dramatic reduction of the greenish color.

While the lanthanum salts of this invention are preferred for use in solutions where removal of metals from hair is desired, they can be used for the treatment of hair not having metallic compounds deposited therein. In all cases, whether removing metal or merely treating hair, the treatment solutions of this invention act to improve the properties of hair and prepare the hair for further treatment as for example in permanent waving of hair.

While the mechanism of the invention is not positively known, it is believed that when exposed to metal ions or compounds of elements such as copper and iron, hair picks up the ions or compounds which are attached thereto. The lanthanum replaces these impurities and can also act to crosslink broken bonds in the hair. This allows color removal by removal of the colored ions or compounds and also acts to improve the structure of hair. As noted in Example 3, the lanthanum acts to reduce swelling by as much as 30%.

The following specific example indicates the improvement in treatment of hair utilizing the method of this invention followed by permanent waving.

EXAMPLE 3

Improved Preperm Treatment

One-gram tresses of white human hair were shampooed either with Agree Shampoo or the shampoo of the formula in Example 1. These tresses were then given permanent waves by a certified cosmetologist.

In the unanimous judgment of many observers, the hair pretreated with the lanthanum-containing shampoo took a markedly better perm than the Agree washed hair as indicated by a tighter, stronger and springier curl.

One explanation of this striking difference is that a statistical analysis of individual hair diameters randomly selected from two populations gave on the average a 10% smaller diameter for the lanthanum-treated tresses.

While specific examples of this invention have been shown and described, many variations are possible. For example, shampoos can be of the liquid or gel type, various formulatives as described above can be used as can others. In all cases, the additives to shampoos or conditioners are such as to avoid interference with the desired lanthanum action.

I claim:

1. A method for removing metal ions or compounds from human hair, comprising
   (a) applying to human hair to which metal ions or compounds have been adsorbed an effective amount of an aqueous solution comprising a water soluble lanthanum salt, said aqueous solution being free of materials that could render said lanthanum salt insoluble or form strong complexes with it;

(b) maintaining said aqueous solution in contact with said human hair for a period of time sufficient to permit said lanthanum salt to desorb said metal ions or compounds from the hair; and (c) removing said desorbed metal ions or compounds from the hair by rinsing the hair with water.

2. The method according to claim 1, wherein the aqueous solution has a pH of from about 3.0 to about 8.3.

3. The method according to claim 1, wherein the concentration of the lanthanum salt is from about 0.04 Normal to saturation.

4. The method according to claim 1, wherein the lanthanum salt is $La_2(SO_4)_3$.

5. The method according to claim 1, wherein the lanthanum salt is $LaCl_3$.

6. The method according to claim 1, wherein the lanthanum salt is in its hydrated form.

7. The method according to claim 6, wherein the hydrated lanthanum salt is $La_2(SO_4)_3 9H_2O$.

8. The method according to claim 1, wherein the aqueous solution is a hair conditioner.

9. The method according to claim 1, wherein the aqueous solution is a shampoo.

10. The method according to claim 9, wherein the shampoo comprises a detergent selected from the group consisting of lauramide DEA, sodium laureth sulfate, sodium lauryl sulfate, triethanolamine lauryl sulfate and ammonium lauryl ether sulfate.

11. The method according to claim 9, wherein the shampoo comprises a chlorine-reducing agent.

12. The method according to claim 11, wherein the chlorine-reducing agent is selected from the group consisting of sodium sulfite, sodium hydrosulfite, sodium thiosulfate, urea, sodium nitrite and ascorbic acid.

* * * * *